United States Patent [19]

Syldatk et al.

[11] 4,150,024
[45] Apr. 17, 1979

[54] REACTION PRODUCTS OF EPSILON-CAPROLACTAM WITH VICINAL HYDROXYALKYLAMINES AND ALKOXYLATION PRODUCTS THEREOF

[75] Inventors: Andreas Syldatk, Dusseldorf; Jens Conrad, Hilden; Harald Schnegelberger; Hans Andree, both of Leichlingen; Günter Jakobi, Hilden, all of Fed. Rep. of Germany

[73] Assignee: Henkel Kommanditgesellschaft auf Aktien, Düsseldorf-Holthausen, Fed. Rep. of Germany

[21] Appl. No.: 860,552

[22] Filed: Dec. 14, 1977

[30] Foreign Application Priority Data

Dec. 17, 1976 [DE] Fed. Rep. of Germany ....... 2657193
Feb. 2, 1977 [AT] Austria ................................... 666/77

[51] Int. Cl.² .......................................... C07D 223/10
[52] U.S. Cl. ............................. 260/239.3 R; 424/244; 252/357
[58] Field of Search .................. 260/239.3 R; 252/357

[56] References Cited

U.S. PATENT DOCUMENTS

| | | | |
|---|---|---|---|
| 2,526,078 | 10/1950 | Kropa et al. | 260/32.6 N |
| 3,945,996 | 3/1976 | Conrad et al. | 260/239.3 R |

FOREIGN PATENT DOCUMENTS

| | | | |
|---|---|---|---|
| 908617 | 10/1962 | United Kingdom | 260/239.3 R |
| 1951225 | 6/1970 | Fed. Rep. of Germany | 260/239.3 R |

OTHER PUBLICATIONS

Stevens, "Polymer Chemistry, an Introduction" (Addison-Wesley), (1975), pp. 194–195, 238–241.

*Primary Examiner*—Natalie Trousof
*Assistant Examiner*—Robert T. Bond
*Attorney, Agent, or Firm*—Hammond & Littell

[57] ABSTRACT

Reaction products of ε-caprolactam with vicinal hydroxyalkylamines and possible adducts thereof with epoxyalkanes having the overall formula:

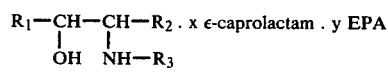

wherein $R_1$ and $R_2$ are members selected from the group consisting of hydrogen and alkyl having 1 to 16 carbon atoms with the proviso that the sum of the carbon atoms in $R_1$ and $R_2$ is from 6 to 30 when $R_1$ and $R_2$ are alkyl and from 6 to 16 when $R_1$ or $R_2$ is hydrogen, $R_3$ is a member selected from the group consisting of hydrogen, alkyl having 1 to 5 carbon atoms and

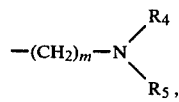

where m is an integer from 2 to 10, and $R_4$ and $R_5$ are members selected from the group consisting of hydrogen and alkyl having 1 to 3 carbon atoms, EPA is an epoxide selected from the group consisting of ethylene oxide, propylene oxide and glycide, x is a number representing mols of from 1 to 5 and y is a number representing mols of from 0 to 5; and the organic and inorganic acid salts thereof; the reaction products are useful as antimicrobials in the treatment of aqueous media and in detergents together with other surface-active compounds.

20 Claims, No Drawings

REACTION PRODUCTS OF EPSILON-CAPROLACTAM WITH VICINAL HYDROXYALKYLAMINES AND ALKOXYLATION PRODUCTS THEREOF

BACKGROUND OF THE INVENTION

Alkylamines as well as N-alkylalkylenediamines both having alkyl radicals of 8 to 18 carbon atoms are known as antimicrobial substances. However, they have adverse dermatological and toxicological properties, which are an obstacle to their use in practice. The reaction products of ε-caprolactam with N-alkylalkylenediamines in the molar ratio of amine to lactam of 1:1 to 1:10 with alkyl radicals with 10 to 18 carbon atoms, which have an excellent activity on bacteria, fungi and algae, have a much better physiological compatibility. These compounds are described and claimed in U.S. Pat. No. 3,892,806. Antimicrobial and algicidal compositions containing the same are described in U.S. Pat. No. 3,977,859. The specific use of the compounds for water preservation is described in U.S. Pat. Nos. 3,874,869 and 3,965,265. These compounds however, are difficultly soluble and in specific systems are not always sufficiently dispersed, so that for some uses, difficulties may occasionally arise.

In U.S. Pat. No. 3,945,996 adducts of the above-named reaction products of ε-caprolactam and N-alkylalkylenediamines with epoxy compounds are disclosed, which adducts have improved solubility. Yet in some cases the antimicrobial activity of these substances leaves something to be desired.

OBJECTS OF THE INVENTION

An object of the present invention is the development of new reaction products of ε-caprolactam with vicinal hydroxyalkylamines and the adducts thereof with $C_2$–$C_3$ epoxyalkanes, the production of these compounds, and their use as antimicrobial agents and also as a component of surfactant mixtures in detergents.

Another object of the present invention is the development of reaction products of ε-caprolactam with vicinal hydroxyalkylamines and possible adducts thereof with epoxyalkanes having the overall formula:

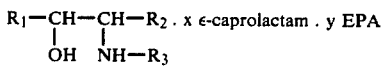

wherein $R_1$ and $R_2$ are members selected from the group consisting of hydrogen and alkyl having 1 to 16 carbon atoms with the proviso that the sum of the carbon atoms in $R_1$ and $R_2$ is from 6 to 30 when $R_1$ and $R_2$ are alkyl and from 6 to 16 when $R_1$ or $R_2$ is hydrogen, $R_3$ is a member selected from the group consisting of hydrogen, alkyl having 1 to 5 carbon atoms and

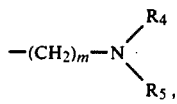

where m is an integer from 2 to 10, and $R_4$ and $R_5$ are members selected from the group consisting of hydrogen and alkyl having 1 to 3 carbon atoms, EPA is an epoxide selected from the group consisting of ethylene oxide, propylene oxide and glycide, x is a number representing mols of from 1 to 5 and y is a number representing mols of from 0 to 5; and the organic and inorganic acid salts thereof.

A further object of the present invention is the development of a process for the production of the above reaction products by reacting 1 mol of the vicinal hydroxyalkylamine with 1 to 5 mols of ε-caprolactam at temperatures of from 180° C. to 250° C. and optionally further reacting the reaction product with 0 to 5 mols of a $C_2$–$C_3$ epoxyalkane at 50° C. to 150° C.

A yet further object of the present invention is to provide a process for the prevention of the growth of microorganisms selected from the group consisting of gram-positive bacteria, gram-negative bacteria, fungi and algae in an aqueous environment, which consists essentially of contacting said microorganisms with an amount effective to prevent the growth of said microorganisms of a reaction product of ε-caprolactam with vicinal hydroxyalkylamines and possible adducts thereof with epoxyalkanes having the overall formula:

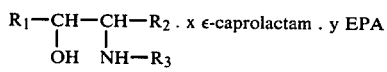

wherein $R_1$ and $R_2$ are members selected from the group consisting of hydrogen and alkyl having 1 to 16 carbon atoms with the proviso that the sum of the carbon atoms in $R_1$ and $R_2$ is from 6 to 30 when $R_1$ and $R_2$ are alkyl and from 6 to 16 when $R_1$ or $R_2$ is hydrogen, $R_3$ is a member selected from the group consisting of hydrogen, alkyl having 1 to 5 carbon atoms and

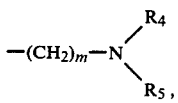

where m is an integer from 2 to 10, and $R_4$ and $R_5$ are members selected from the group consisting of hydrogen and alkyl having 1 to 3 carbon atoms, EPA is an epoxide selected from the group consisting of ethylene oxide, propylene oxide and glycide, x is a number representing mols of from 1 to 5, and y is a number representing mols of from 0 to 5; and the organic and inorganic acid salts thereof.

A still further object of the present invention is to provide a surfactant mixture composition consisting essentially of at least one surface-active compound selected from the group consisting of anionic surface-active compounds, nonionic surface-active compounds and zwitterionic surface-active compounds, in combination with a reaction product of ε-caprolactam with vicinal hydroxyalkylamines and possible adducts thereof with epoxyalkanes having the overall formula:

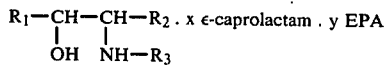

wherein $R_1$ and $R_2$ are members selected from the group consisting of hydrogen and alkyl having 1 to 16 carbon atoms with the proviso that the sum of the carbon atoms in $R_1$ and $R_2$ is from 6 to 30 when $R_1$ and $R_2$ are alkyl and from 6 to 16 when $R_1$ or $R_2$ is hydrogen, $R_3$ is a member selected from the group consisting of hydrogen, alkyl having 1 to 5 carbon atoms and

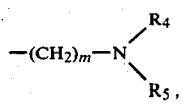

where m is an integer from 2 to 10, and $R_4$ and $R_5$ are members selected from the group consisting of hydrogen and alkyl having 1 to 3 carbon atoms, EPA is an epoxide selected from the group consisting of ethylene oxide, propylene oxide and glycide, x is a number representing mols of from 1 to 5, and y is a number representing mols of from 0 to 5; and the organic and inorganic acid salts thereof; the weight ratio of said at least one surface-active compound to said reaction product being from 50:1 to 2:1.

These and other objects of the invention will become more apparent as the description thereof proceeds.

DESCRIPTION OF THE INVENTION

The subject matter of the present invention is novel reaction products having the overall formula I:

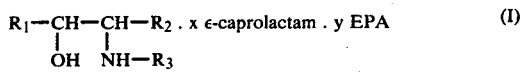

consisting of the reaction products of ε-caprolactam with vicinal hydroxyalkylamines, and of the compounds obtained by addition of a short-chain epoxyalkane to these reaction products, where $R_1$ and $R_2$ in formula I each represent an alkyl group with 1 to 16 carbon atoms or hydrogen, and the sum of the carbon atoms of these alkyl groups is in the range of 6 to 30, preferably 8 to 18, and in the case where $R_1$ or $R_2$=H, the existing alkyl group $R_1$ or $R_2$ has 6 to 16 carbon atoms, $R_3$ being hydrogen, an alkyl group with 1 to 5 carbon atoms, or the group:

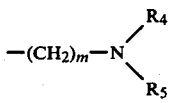

with m=2 to 10, more particularly 2 to 6, and $R_4$ and $R_5$ are hydrogen or an alkyl group with 1 to 3 carbon atoms, EPA is a mol of an epoxyalkane from the group of ethylene oxide, propylene oxide and glycide, and x is a mol number between 1 and 5, more particularly between 1.5 and 3.5, and y is a mol number between 0 and 5, more particularly between 0.5 and 5. The invention also relates to the inorganic and organic acid addition salts of the reaction products.

More particularly, the present invention relates to reaction products of ε-caprolactam with vicinal hydroxyalkylamines and possible adducts thereof with epoxyalkanes having the overall formula:

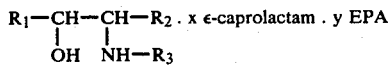

wherein $R_1$ and $R_2$ are members selected from the group consisting of hydrogen and alkyl having 1 to 16 carbon atoms with the proviso that the sum of the carbon atoms in $R_1$ and $R_2$ is from 6 to 30 when $R_1$ and $R_2$ are alkyl and from 6 to 16 when $R_1$ or $R_2$ is hydrogen, $R_3$ is a member selected from the group consisting of hydrogen, alkyl having 1 to 5 carbon atoms and

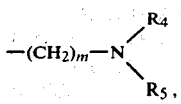

where m is an integer from 2 to 10, and $R_4$ and $R_5$ are members selected from the group consisting of hydrogen and alkyl having 1 to 3 carbon atoms, EPA is an epoxide selected from the group consisting of ethylene oxide, propylene oxide and glycide, x is a number representing mols of from 1 to 5 and y is a number representing mols of from 0 to 5; and the organic and inorganic acid salts thereof.

The new reaction products are obtained by reaction of ε-caprolactam with a vicinal hydroxyalkylamine of formula II:

wherein $R_1$ and $R_2$ each represent an alkyl group with 1 to 16 carbon atoms or hydrogen, and the sum of the carbon atoms in $R_1$ and $R_2$ is in the range of 6 to 30, preferably 8 to 18, and more particularly 9 to 16, and in the case where $R_1$ or $R_2$=H, the existing alkyl group has 6 to 16 carbon atoms, and $R_3$ is hydrogen, an alkyl group with 1 to 5 carbon atoms, more particularly methyl, or the group:

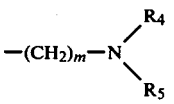

with m=2 to 10, more particularly 2 to 6, and $R_4$ and $R_5$ signify hydrogen or alkyl with 1 to 3 carbon atoms, more particularly methyl, 1 mol of the hydroxyalkylamine being allowed to react with 1 to 5 mols of ε-caprolactam for 3 to 20 hours at temperatures from 180° C. to 250° C., and the reaction product being optionally reacted further with 0.5 to 5 mols of ethylene oxide, propylene oxide or glycide at 50° C. to 150° C. The alkyl groups $R_3$, $R_4$ and $R_5$ in the reaction product of formula I are preferably methyl groups.

The new compounds of formula I are distinguished by improved antimicrobial activity. In addition, they increase the washing effect of surface-active compounds or mixtures of surface-active compounds. More particularly, the present invention also relates to a process for the prevention of the growth of microorganisms selected from the group consisting of gram-positive bacteria, gram-negative bacteria, fungi and algae in an aqueous environment, which consists essentially of contacting said microorganisms with an amount effective to prevent the growth of said microorganisms of a reaction product of ε-caprolactam with vicinal hydroxyalkylamines and possible adducts thereof with epoxyalkanes having the overall formula:

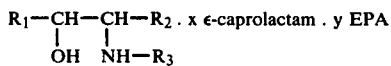

wherein $R_1$ and $R_2$ are members selected from the group consisting of hydrogen and alkyl having 1 to 16 carbon atoms with the proviso that the sum of the carbon atoms in $R_1$ and $R_2$ is from 6 to 30 when $R_1$ and $R_2$ are alkyl and from 6 to 16 when $R_1$ or $R_2$ is hydrogen, $R_3$ is a member selected from the group consisting of hydrogen, alkyl having 1 to 5 carbon atoms and

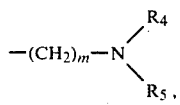

where m is an integer from 2 to 10, and $R_4$ and $R_5$ are members selected from the group consisting of hydrogen and alkyl having 1 to 3 carbon atoms, EPA is an epoxide selected from the group consisting of ethylene oxide, propylene oxide and glycide, x is a number representing mols of from 1 to 5, and y is a number representing mols of from 0 to 5; and the organic and inorganic acid salts thereof, as well as a surfactant mixture composition consisting essentially of at least one surface-active compound selected from the group consisting of anionic surface-active compounds, nonionic surface-active compounds and zwitterionic surface-active compounds, in combination with a reaction product of ε-caprolactam with vicinal hydroxyalkylamines and possible adducts thereof with epoxyalkanes having the overall formula:

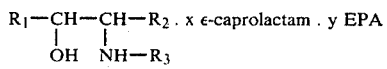

wherein $R_1$ and $R_2$ are members selected from the group consisting of hydrogen and alkyl having 1 to 16 carbon atoms with the proviso that the sum of the carbon atoms in $R_1$ and $R_2$ is from 6 to 30 when $R_1$ and $R_2$ are alkyl and from 6 to 16 when $R_1$ or $R_2$ is hydrogen, $R_3$ is a member selected from the group consisting of hydrogen, alkyl having 1 to 5 carbon atoms and

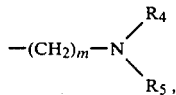

where m is an integer from 2 to 10, and $R_4$ and $R_5$ are members selected from the group consisting of hydrogen and alkyl having 1 to 3 carbon atoms, EPA is an epoxide selected from the group consisting of ethylene oxide, propylene oxide and glycide, x is a number representing mols of from 1 to 5, and y is a number representing mols of from 0 to 5; and the organic and inorganic acid salts thereof; the weight ratio of said at least one surface-active compound to said reaction product being from 50:1 to 2:1.

The production of the reaction products of ε-caprolactam with the hydroxyalkylamines occurs expediently in the melt by heating a mixture defined by the above-named ratio of the reaction partners to 180° C. to about 250° C., preferably under nitrogen, with reaction times between three and 20 hours being employed. The reaction products are then obtained as water-clear, thin melts. With respect to the antimicrobial properties, it has been found to be advantageous if the molar ratio of hydroxyalkylamine to ε-caprolactam in the reaction products is 1:2 to 1:3.

For the production of the hydroxyalkylamines of formula II serving as starting products for the reaction with ε-caprolactam, non-terminal or terminal alkenes or olefins are reacted with epoxidizing agents, such as peracetic acid to give the respective olefin epoxides or epoxyalkanes. By further reaction with ammonia, primary alkylamines, alkylenediamines whose alkylene groups contain 2 to 6 carbon atoms, N-alkylalkylenediamines or N,N-dialkylalkylenediamines, the corresponding vicinal hydroxyalkylamine of formula II is formed. The reactions for the production of the vicinal hydroxyalkylamines of formula II and some of the compounds of formula II are described in U.S. patent applications Ser. No. 683,319, filed May 5, 1976, now abandoned; Ser. No. 683,322, filed May 5, 1976, and Ser. No. 715,520, filed Aug. 18, 1976, now abandoned.

In the preparation of the vicinal hydroxyalkylamines of formula II, preferably, terminal mono-olefins with 10 to 18 carbon atoms or mixtures of mono-olefins with 10 to 18 carbon atoms containing statistically distributed non-terminal double bonds are employed. These olefin mixtures are known per se and can be obtained, for example by catalytic dehydration or by chlorination/-dehydrochlorination of paraffins having 8 to 24 carbon atoms and selective extraction of the non-terminal monoolefins obtained. However, it is also possible to use mixtures of such olefins with saturated hydrocarbons, as they are obtained in the preparation of these olefins. Preferred as mixtures of isomeric monoolefins are the fractions with a high content of linear $C_{11-14}$ olefins or $C_{15-18}$ olefins. The particularly preferred mixtures of non-terminal olefins have the following chain length distribution:

| (a) Fraction $C_{11-14}$ olefins (distribution in % by weight) | | |
|---|---|---|
| $C_{11}$ | Olefins | About 22 |
| $C_{12}$ | " | " 30 |
| $C_{13}$ | " | " 26 |
| $C_{14}$ | " | " 22 |
| (b) Fraction $C_{15}$–$C_{18}$ olefins | | |
| $C_{15}$ | Olefins | About 26 |
| $C_{16}$ | " | " 35 |
| $C_{17}$ | " | " 31 |
| $C_{18}$ | " | " 6 |

The above preferred mixtures of $C_{11}$–$C_{14}$ olefins and $C_{15}$–$C_{18}$ olefins can also have deviations in the indicated chain length distributions.

For the preparation of the products according to the invention, the olefin mixtures are epoxidized by means of known methods, for example, with peracetic acid.

Terminal olefins can likewise be reacted to obtain the epoxyalkanes having 10 to 18 carbon atoms, such as 1,2-epoxydecane, 1,2-epoxydodecane, 1,2-epoxytridecane, 1,2-epoxytetradecane, 1,2-epoxyhexadecane and 1,2-epoxyoctadecane. Mixtures of these 1,2-epoxyalkanes can also be employed.

If the reaction products of hydroxyalkylamine and ε-caprolactam are to be further reacted with an epoxyalkane, e.g., ethylene oxide, propylene oxide or glycide, this is done in the usual manner, preferably at elevated temperatures of 50° C. to 150° C. The addition of the epoxide is carried out expediently immediately following the lactam/amine reaction, by letting the calculated quantity of epoxide act on the melt of the reaction product. The quantity ratio of the reaction partners is selected so that the molar ratio of hydroxyalkylamine to epoxyalkane is 1:0.5 to 1:5, preferably 1:1 to 1:3. Preferably ethylene oxide is the epoxyalkane employed. The reaction products thus obtained are colorless to yellow masses, generally oily to pasty at room temperature, which have satisfactory solubility in organic solvents, such as alcohols, ketones, esters, chlorinated hydrocarbons, and also in water. By adding equimolar quantities of inorganic or organic acids, such as sulfuric acic, phosphoric acid, formic acid, acetic acid, lactic acid, tartaric acid, citric acid, following the reaction, the corresponding acid addition salts can be produced, which have good solubility in water.

The compounds of formula I according to the invention have very good microbistatic and microbicidal actions against gram-positive and gram-negative bacteria and fungi and also a very good inhibiting action on algae. Due to their very good dermatological compatibility and low toxicity, they are excellently suited for solving a variety of technical disinfection and preservation problems. As examples of such applications should be named their use as disinfectants in household cleaners; in industrial cleaning agents for food plants, dairies, breweries; in area disinfectants for hospitals; for laundry disinfection in the usual washing processes and in dry cleaning; as preservatives for cosmetics; as preservatives for adhesives based on cellulose, starch and animal protein; as preservatives for dispersion dyes, metal treatment oils; as a disinfectant and preservative for a variety of service waters as, for example, in cooling systems, swimming pools, scrubbers of air conditioning systems; also as a deodorant in deodorizing soaps.

The invention, therefore, relates to the use of the reaction products of formula I of the invention in liquid, pasty or solid preparations which contain these substances in quantities of 0.1% to 5% by weight, preferably 0.5% to 3% by weight, based on the total weight. When used for the preservation of industrial water, 0.5 to 50 mg preferably 1 to 10 mg, of the reaction product of the invention per liter of industrial or service water to be treated is employed. In packaging for a variety of applications the substances of the invention can be combined with other additives such as surface-active compounds, water softeners, rust preventatives, complex-formers, thickeners, bases, acids, perfumes, foam inhibitors, solvents and the like.

The use of the reaction products of the invention for the preservation of industrial and utility water occurs expediently in combination with phosphonic acids or their water-soluble salts as complex-formers. In particular, alkanediphosphonic acids or phenylmethanediphosphonic acids substituted in the 1-position with hydroxyl or an amino group, aminotrialkylene-triphosphonic acids, alkylenediaminetetraalkylene-tetraphosphonic acids, or phosphonoalkanedi- or tricarboxylic acids can be employed.

Suitable phosphonic acids are, for example:
1-hydroxyethane-1,1-diphosphonic acid,
1-hydroxypropane-1,1-diphosphonic acid
1-hydroxybutane-1,1-diphosphonic acid 1-hydroxypentane-1,1-diphosphonic acid
1-hydroxyhexane-1,1-diphosphonic acid
1-hydroxy-1-phenylmethane-1,1-diphosponic acid
1-aminoethane-1,1-diphosphonic acid
1-amino-1-phenylmethane-1,1-diphosphonic acid
1-(dimethylamino)-ethane-1,1-diphosphonic acid
1-(dimethylamino)-butane-1,1-diphosphonic acid
diethylaminomethane-diphosphonic acid
propylaminomethane-diphosphonic acid
butylaminomethane-diphosphonic acid
amino-tri-(methylene-phosphonic acid)
ethylenediamine-(tetra-methylene-phosphonic acid)
diethylenetriaminepenta-(methylene-phosphonic acid)
amino-(2-propylene-2-phosphonic acid)
phosphono-succinic acid
1-phosphono-1-methylsuccinic acid
2-phosphonobutane-1,2,4-tricarboxylic acid.

The water-soluble salts of said phosphonic acids also enter into consideration, in particular, their sodium, potassium, ammonium or alkanolamine salts. The phosphonic acids may be used singly or in admixture. Particularly successful has been a mixture of 1-hydroxyethane-1,1-diphosphonic acid and aminotri-(methylene-phosphonic acid) in the weight ratio of 4:1 to 1:4.

The phosphonic acids or their water-soluble salts are contained in the ready made up preservative agent for industrial and utility water in such a quantity that they contain per liter of the water to be treated 0.2 mg up to 1½ times the quantity required for the complete complexing of the hardness formers present in the system. The weight ratio between phosphonic acid component and biocide component may be between 1:10 to 10:1. Preferably, however, a ratio of 3:1 to 1:3 is used. The water treated with the agents of the invention should have a content of biocide between 0.5 and 50 gm per cubic meter and a content of phosphonic acid between 0.2 and 20 gm per cubic meter.

Suitable corrosion inhibitors for combination with the reaction products of the invention in water preservatives are, for example, water-soluble orthophosphates, such as mono-, di- or tri-alkali metal phosphates. Furthermore, water-soluble zinc salts, such as zinc sulfate or zinc nitrate may be used, which can be added instead of the orthophosphates, but preferably simultaneously with the orthophosphates. Other inhibitors which may likewise be used if desired are alkali metal nitrites, such as potassium or more particularly sodium nitrite. An addition of alkali metal silicates such as potassium or sodium silicate is also possible. The inhibitors are added in amounts of 0.5 to 200 mg/liter, preferably 1 to 50 mg/l. The individual additives may be processed to solid mixtures. Alternatively, however, solutions thereof may be produced, which are supplied to the water in the desired quantity. There is no difficulty in adjusting the pH of these products either by additional supply of alkali metal hydroxide or carbonate or by selection of a suitable mono-, di- or trialkali metal phosphate in such a way that simultaneously a certain pH regulation of the treated water can be achieved at the same time, if this is desired or required.

The advantages of the combination of the reaction products of the invention with the phosphonic acid components consists, among others, in the intensified synergistic attack of the biocide on the biological material and the microorganisms. This attack leads to very rapid degradation of their growth. Conversely, the dispersing effect of the phosphonic acids as well as their anticorrosive effect are reciprocally enhanced by the biocide component. Due to the very small proportions both of the phosphonic acid component and of the biocide component, the load on the sewage system is minimal. Because of the adsorption of the biocide component by the biological material, moreover, the noxious content in the sewage system is further reduced. In addition, the biocide component is biodegradable at appropriate dilution.

Surprisingly, it was found further that even with a small quantity of the reaction products of formula I together with a surface-active compound (tenside) or tenside mixture in detergents brings about a synergistic increase of the washing power which is effective in particular in cold water washing solutions. As is known, until now it has been necessary to wash with a warm water washing solution in order to obtain a satisfactory result. The availability of hot water from water heaters or through washing machines with heating elements is, therefore, not only a precondition for a good result, but also a major cost factor in laundering. In recent times it has been found that because of changed consumer habits and because of the predominance of easy-care textiles of synthetic fibers, the former boiling washing is being replaced more and more by washing at 60° C. in Europe and almost completely in the United States, which undoubtedly helps to save energy. However, in order to save more thermal energy in washing and to be able to wash with good results also in those cases where only cold water is available, a cold-water detergent had to be developed which washes well also with unheated water, i.e., water of 10° C. to 30° C., more particularly 15° C. to 25° C., as it usually comes out of the tap. This problem is solved by the use, according to the invention, of compounds of formula I as a constituent of tenside mixtures in detergents.

The subject of the invention is, therefore, also the use of compounds of formula I as a constituent of surface-active compound or tenside mixtures in combination with at least one surface-active compound from the group of the anionic, surface-active compounds, nonionic surface-active compounds and zwitterionic surface-active compounds in detergents, the ratio by weight of the other tensides to the reaction product of formula I being 50:1 to 2:1 and more particularly 30:1 to 2:1. The cold water detergents contain the combination of tenside or tenside mixture and reaction product of formula I in amounts of from 5% to 50% by weight. The remaining 50% to 95% by weight of the cold water detergent consists of at least one additional conventional detergent constituent. Accordingly, the detergents of the invention generally contain from 0.1% to 2.5%, preferably 0.3% to 2.5% by weight, of the reaction product of Formula I.

As conventional detergent constituents enter into consideration, those of the group of the inorganic and/or organic builders, foam inhibitors, optical brighteners, soil suspension agents, enzymes, dyes, perfumes and water. Liquid forms may contain in addition to or instead of water, low-molecular-weight organic solvents miscible with water, in particular from the group of the alkanols, alkanediols, alkoxyalkanols and alkoxyalkoxyalkanols.

With the detergent of the invention the usual washing operations can be carried out with good results for manual washing and for machine washing with cold water as it is directly available from the tap. The agents of the invention may also contain bleaching additives, consisting of peroxy compounds as active oxygen carriers, in particular sodium perborate, stabilizers and activators. Even, in the absence of the activators, an additional bleaching effect is achieved in washing at elevated temperatures, e.g., in 60° C. washing to boiling washing. Also when washing at these elevated temperatures in the washing machine, the reaction products of formula I used according to the invention contribute in advantageous manner to the total washing effect. In these all-temperature detergents the bleaching addition of peroxy compound, stabilizer and activator for the peroxy compound amounts to 10% to 40% by weight, more particularly 15% to 35% by weight of the total detergent.

The washing power-intensifying effect of the compounds of formula I is manifest in particular when they are used in detergents which contain at least one tenside from the group of the alkylbenzene sulfonates, the alkane sulfonates, and the $\alpha$-sulfofatty acid esters alone or in combination with tensides of the type of the fatty alcohol sulfates, fatty alcohol glycol ether sulfates and/or the ethoxylated $C_{8-22}$ alkanols or alkenols as a tenside component. In these compositions the compounds of formula I are present in quantities of 0.3% to 2.5% by weight together with the tenside component, this tenside component being present in an amount sufficient to adjust a weight ratio of tenside component to comound of formula I in the range of 30:1 to 2:1, more particularly 20:1 to 5:1, and the remaining constituents of the agent, in particular powdery and/or liquid vehicles from the group of the powdery organic and inorganic builders, the water-soluble lower alkanols, alkanediols, alkoxyalkanols and alkoxyalkoxyalkanols and water, optionally including a bleach component, being present in a quantity of amount of 50% to 95% by weight, more particularly from 55% to 90% by weight of the detergent.

Preferably conventional additives from the group of the foam inhibitors, optical brighteners, soil suspension agents, enzymes, dyes and perfumes are also present in the detergents of the invention, in a total amount of from 0.5% to 10% by weight.

Detergents of the invention which show a particularly marked washing capacity at cold temperatures as well as at elevated or boiling temperatures preferably contain, as the tenside component, a sulfonate surface-active compound of the above stated type together with a nonionic surface-active compound of the type of the ethoxylated aliphatic $C_{10}$–$C_{20}$ alcohols, and as the washing power-intensifying additive, the reaction product of formula I in which the mol number x is within the range of 1.5 to 3.5, more particularly 2, y is a number from 1 to 4, and EPA signifies added ethylene oxide.

Preparations of the invention whose tenside component consists exclusively of nonionic tensides, more particularly of ethoxylated aliphatic $C_{10}$–$C_{20}$ alcohols, are likewise preferred. The aliphatic $C_{10}$–$C_{20}$ alcohols are preferably alkanols and alkenols having 10 to 20 carbon atoms.

A particularly good washing effect is observed when these nonionic ethoxylation products are present as mixtures of products of different average ethoxylation degree and when in this mixture, the ratio of the addition products of 8 to 20 mols of ethylene oxide to 1 mol of an aliphatic $C_{10}$–$C_{20}$ alcohol to the ethoxylation products with 2 to 7 mols of ethylene glycol per mol of alcohol is 5:1 to 1:3.

Detergents of the invention with weak foaming capacity contain additionally from 0.2% to 0.8% by weight of a non-surface-active type foam inhibitor or from 0.5% to 5% by weight of an alkali metal soap consisting essentially of $C_{18}$–$C_{22}$ fatty acids, or a mixture of the non-surface-active type foam inhibitor and the soap in an amount of from 0.2% to 5% by weight.

The detergents of the invention are prepared as powdery, pasty or liquid preparations. In the case of the powders, which are preferred, the vehicles consist of powdery organic and inorganic builders, which may be water-soluble or water-insoluble and which consist at least in part of substances which exert on the hardness formers of the water a complexing and/or precipitating action. The terms "powdery vehicles" and "builders" comprise also an optionally present active oxygen-yielding bleaching component.

The manufacture of pourable preparations in powdery form can be effected by the usual methods, e.g., by cold and hot spray drying. Alternatively, the active substances of formula I, which at room temperature are usually liquid or pasty, may be applied onto the powdery particles of the remaining constituents of the preparation, in particular, by spraying onto a portion of the builders, for which purpose sodium tripolyphosphate and sodium sulfate with bulk weights of 200 to 500 gm/l are especially suitable as vehicles or, in the case of bleach-containing preparations, by spraying the reaction product of formula I on finely pulverized sodium perborate.

The liquid-to-pasty preparations are preferably manufactured by dissolving the tenside component in the solvent serving as liquid vehicle, then adding the reaction product of formula I and homogenizing the mixtures by stirring and possibly heating and mixing in possibly planned additional components.

If the wash solution contains a peroxy compound as bleaching agent, a desired bleaching effect on the textiles can be achieved following the washing in cold solution by heating this solution to temperatures of preferably 60° to 95° C. for a period of 5 to 30 minutes.

There follows now a more detailed description of the most important constituents contained in the detergents of the invention, arranged by substance classes.

The surface-active compounds or tensides contain in the molecule at least one hydrophobic organic radical and a water-solubilizing anionic, zwitterionic or nonionic group. The hydrophobic radical is usually an aliphatic hydrocarbon radical with 8 to 26, preferably 10 to 22 and more particularly 12 to 18 carbon atoms, or an alkylaromatic radical such as alkyl phenyl and alkylnaphthyl with 6 to 18, preferably 8 to 16 aliphatic carbon atoms.

The anionic surface-active compounds which can be used are, for example, soaps from natural or synthetic, preferably saturated fatty acids, more particularly of the chain lengths of 12 to 18 carbon atoms, possibly also from resinic or naphthenic acids. Suitable synthetic anionic surface-active compounds are those of the type of the sulfonates, sulfates and synthetic carboxylates.

The sulfonate type of anionic surface-active compounds are, for example, benzenesulfonates ($C_{9-15}$-alkyl), olefin sulfonates, i.e., mixtures of alkene and hydroxyalkane sulfonates as well as alkanedisulfonates, as are obtained, for example, from $C_{12}-C_{18}$-mono-olefins with a terminal or non-terminal double bond by sulfonation with gaseous sulfur trioxide and subsequent alkaline or acid hydrolysis of the sulfonation products. Suitable also are the alkane sulfonates obtainable from $C_{12}-C_{18}$ alkanes by sulfochlorination or sulfoxidation and subsequent hydrolysis or neutralization or, respectively, by bisulfite addition to olefins, also the esters of $\alpha$-sulfofatty acids, e.g., the $\alpha$-sulfonated methyl or ethyl esters of hydrogenated coconut, palm kernel, or tallow fatty acids.

Suitable tensides of the sulfate type are the sulfuric acid monoesters of primary alkanols and/or alkenols having 10 to 20 carbon atoms (e.g., from coconut fatty alcohols, tallow fatty alcohols or oleyl alcohol) and those of secondary alkanols. Further suitable are the sulfated fatty acid alkanol amides, sulfated fatty acid mono-glycerides or sulfated reaction products of 1 to 4 mols of ethylene oxide with the primary or secondary fatty alcohols or alkylphenols.

Further suitable anionic tensides are the fatty acid esters or amides of hydroxy or amino carboxylic acids or sulfonic acids, e.g., the fatty acid sarcosides, glycolates, lactates, taurides or isethionates.

The anionic surface-active compounds may be present in the form of their alkali metal salts, such as sodium, potassium, etc. and ammonium salts and also as soluble salts of organic bases, such as mono-, di or triethanolamine.

The nonionic surface-active compounds or tensides are usually addition products of 1 to 40, preferably 2 to 20, mols of ethylene oxide to 1 mol of an aliphatic compound containing essentially 10 to 20 carbon atoms from the group of the alcohols, alkylphenols, carboxylic acids, fatty amines, carboxylic acid amides or alkanesulfonamides. Especially important are the addition products of 8 to 20 mols of ethylene oxide to primary $C_{10}-C_{20}$ alkanols and/or alkenols, as for example, to coconut or tallow fatty alcohols, to oleyl alcohol, to oxo-alcohols, or to secondary alkanols of this chain length, also to mono- or di-alkylphenols with 6 to 14 carbon atoms in the alkyl(s). Apart from these water-soluble nonionics, also the insoluble or not completely water-soluble polyglycol ethers of these alcohols and alkylphenols with 2 to 7 ethylene glycol ether units in the molecule are of interest, especially when used together with water-soluble nonionic or anionic tensides.

Also usable as nonionic tensides are the water-soluble addition products, containing 20 to 35 ethylene glycol ether groups and 10 to 100 propylene glycol ether groups, of ethylene oxide to polypropylene glycol, alkylenediaminepolypropylene glycol and to alkylenepolypropylene glycols with 1 to 10 carbon atoms in the alkyl chain. In these adducts, the polypropylene glycol chain functions as hydrophobic radical. Also nonionic tensides of the type of the aminoxides or sulfoxides are usuable, for example, N-coconut-alkyl-N,N-dimethylaminoxide, N-hexadecyl-N,N-bis(2,3-dihydroxypropyl)-aminoxide, N-tallow-alkyl-N,N-dihydroxy-ethylaminoxide.

The term "nonionic tensides (Nonionics)", however, does not comprise the active substances of formula I used according to the invention which can only contain a maximum of 5 alkoxy units.

The zwitterionic surface-active compounds or tensides are preferably derivatives of aliphatic quaternary ammonium compounds, in which one of the aliphatic radicals consists of a $C_8-C_{18}$ radical, preferably alkyl or alkenyl having 8 to 18 carbon atoms, and another contains an anionic water-solubilizing carboxy, sulfo and sulfato group. Typical representatives of such surface-active betaines are, for example:

3-(N-hexadecyl-N,N-methylammonio)-propanesulfonate 3-(N-tallow-alkyl-N,N-dimethylammonio)-2-hydroxypropanesulfonate 3-[N-hexadecyl-N,N-bis-(2-hydroxyethyl)-ammonio]-2-hydroxypropanesulfate 3-[N-coconut alkyl-N,N-bis-(2,3-dihydroxypropyl)-ammonio]-propanesulfonate N-tetradecyl-N,N-dimethylammonioacetate N-hexadecyl-N,N-bis-(2,3-dihydroxypropyl)-ammonioacetate.

The foaming tendency of the tensides can be increased or decreased by combination of suitable tenside types. A reduction can be achieved also by additions of non-surface-active organic substances. A reduced tendency to foaming, which is desirable for machine washing, is often obtained by combining different tenside types, for example, sulfates and/or sulfonates with Nonionics and/or soaps. The foam-reducing effect of the soaps increases with the degree of saturation and the carbon number of the fatty acid radical. The foam-inhibiting soaps which are suitable, therefore, are soaps of natural or synthetic origin which have a high proportion of $C_{18}$-$C_{22}$ fatty acids, for example, the derivatives of hydrogenated train oils and rapeseed oils. In practice, generally fatty acid mixtures with a chain length distribution of $C_{12}$ to $C_{22}$ are employed. The expression "soaps of fatty acids with essentially $C_{18}$-$C_{22}$ carbon atoms" is meant to include soaps of which at least 50% by weight consist of $C_{18}$-$C_{22}$ fatty acid salts. The combination of foam-reducing soaps with non-surface-active foam inhibitors is suitable above all for regulating the foaming in washing machines during the actual washing and during rinsing.

The non-surface-active foam inhibitors involve generally water-insoluble, usually aliphatic compounds containing $C_8$-$C_{22}$ carbon radicals. Suitable non-surface-active foam inhibitors are, for example, the N-alkylaminotriazines, i.e., reaction products of 1 mol of cyanuric chloride with 2 to 3 mols of a mono- or dialkylamine having essentially 8 to 18 carbon atoms in the alkyl(s). Also suitable are propoxylated and/or butoxylated aminotriazines, e.g. the reaction products of 1 mol of melamine with 5 to 10 mols of propylene oxide and additionally 10 to 50 mols of butylene oxide as well as the aliphatic $C_{18}$-$C_{40}$ ketones or alkanones, such as stearone, the fatty ketones from hardened train oil fatty acid or tallow fatty acid, etc., also the paraffins and halogen paraffins with melting points below 100° C. and silicone oil emulsions based on polymeric silicon-organic compounds.

The organic and inorganic builders are suitable weakly acid, neutral or alkaline reacting salts, in particular, alkali metal salts which are able to precipitate or to complex calcium ions. The inorganic salts of importance are the water-soluble alkali metal meta-phosphates or alkali metal poly-phosphates, in particular, pentasodium tripolyphosphate, as well as the alkali metal orthophosphates and alkali metal pyrophosphates. These phosphates may be wholly or partially substituted by organic complex formers for calcium ions. These include compounds of the type of the aminopolycarboxylic acids, such as nitrilotriacetic acid, ethylenediaminetetraacetic acid, diethylenetriaminepentaacetic acid and higher homologues. Suitable phosphorus-containing organic complex formers are the water-soluble salts of the alkanepolyphosphonic acids, aminoalkanepolyphosphonic acids and hydroxyalkanepolyphosphonic acids and phosphonoalkanepolycarboxylic acids, such as methanediphosphonic acid, dimethylaminomethane-1,1-diphosphonic acid, aminotri-(methylenetriphosphonic acid), 1-hydroxyethane-1,1-diphosphonic acid, 1-phosphonoethane-1,2-dicarboxylic acid, 2-phosphonobutane-1,2,4-tricarboxylic acid, etc.

Organic builders of special importance are the nitrogen and phosphorus-free polycarboxylic acids forming complex salts with calcium ions, which also include polymers containing carboxyl groups. Suitable, for example, are citric acid, tartaric acid, benzene-hexacarboxylic acid and tetrahydrofurane-tetracarboxylic acid. Also polycarboxylic acids containing ether groups are usable, such as 2,2'-oxydisuccinic acid, as well as polyhydric alcohols or hydroxycarboxylic acids partially or completely etherified with glycolic acid, for example, biscarboxymethylethylene glycol, carboxymethyloxysuccinic acid, carboxymethyltartronic acid and carboxymethylated or oxidized polysaccharides. Further suitable are the polymeric-carboxylic acids having a molecular weight of at least 350 in the form of water-soluble salts, as, for example, the alkali metal salts of polyacrylic acid, poly-$\alpha$-hydroxyacrylic acid, polymaleic acid, as well as the copolymers of the corresponding monomeric carboxylic acids with one another or with ethylenically-unsaturated compounds such as ethylene, propylene, isobutylene, vinylmethyl ether or furan.

Water-insoluble inorganic builders are also suitable such as the finely divided, synthetically prepared water-insoluble silicates described more specifically in U.S. patent application Ser. No. 458,306, filed Apr. 5, 1974, now abandoned, and its continuation Ser. No. 800,308, filed May 25, 1977, as phosphate substitutes for washing and cleaning agents, of the general formula

$$0.7-1.5 \text{Kat}_{2/n}\text{O}.\text{Me}_2\text{O}.0.8-6 \text{ SiO}_2,$$

where Kat is a cation of valence n, exchangeable with the calcium ion, and Me is aluminum or boron, which additionally contain combined water and have a calcium binding power of 50 to 200 mg CaO/gm of the anhydrous silicate. Preferably, the alkali metal aluminosilicates of this composition are employed, in particular, the crystalline sodium aluminosilicates of the composition

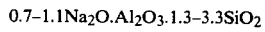

$$0.7-1.1\text{Na}_2\text{O}.\text{Al}_2\text{O}_3.1.3-3.3\text{SiO}_2$$

whose calcium binding power lies in the range of 100 to 200 mg CaO/gm of the anhydrous aluminosilicate, the particle sizes of these aluminosilicates being essentially below 40$\mu$ and more particularly in the range of 10 to 0.1$\mu$. The determination of the calcium binding power is explained in the above-identified application.

Suitable inorganic, non-complexing salts which can be employed are the bicarbonates, carbonates, borates, sulfates or silicates of the alkali metals, also called "wash alkalis;" from the alkali metal silicates, especially the sodium silicates with a ratio $Na_2O:SiO_2$ of 1:1 to 1:3.5 are useful.

Other builders which because of their hydrotropic properties are used mostly in liquid detergent compositions are the salts of the non-surface-active sulfonic acids, carboxyl acids and sulfocarboxylic acids containing 2 to 9 carbon atoms, for example, the alkali metal salts of alkane sulfonic acids, benzene sulfonic acid, toluene sulfonic acid, xylene sulfonic acid or cumenesulfonic acid, of sulfobenzoic acids, sulfophthalic acid, sulfoacetic acid, sulfosuccinic acid, as well as the salts of acetic acid or lactic acid. Acetamide and urea are also suitable as solution aids due to their hydrotropic properties.

The preparations may also contain soil suspension agents which maintain the dirt that is detached from the fiber, suspended in the bath and thus prevent graying or redeposition of the soil. The water-soluble colloids, usually of an organic nature, are suitable for this purpose as, for example, the water-soluble salts of polymeric carboxylic acids, glue, gelatines, salts of ether carboxylic acids or ether sulfonic acids of starch or cellulose or salts of acid sulfuric acid esters of cellulose or of starch. Also water-soluble polyamides containing acid groups are suitable for this purpose. Further, soluble starch preparations and starch products other than those named above, as for example, degraded starch, aldehyde starches, etc. can be used. Polyvinyl pyrrolidone is also usable. Alkali metal carboxymethylcelluloses are preferable, however, as soil suspension agents.

Among the compounds serving as bleaches and yielding $H_2O_2$ in water, sodium perborate-tetrahydrate ($NaBO_2.H_2O_2.3H_2O$) and the monohydrate ($NaBO_2.H_2O_2$) are of special importance. But also other borates yielding $H_2O_2$ are usable, such as perborax, $Na_2B_4O_7.4H_2O_2$. These compounds may be replaced partially or completely by other active oxygen carriers, in particular, by peroxyhydrates, such as peroxycarbonates ($Na_2CO_3.1.5H_2O_2$) peroxypyrophosphates, citrate perhydrates, urea-$H_2O_2$ or melamine-$H_2O_2$ compounds as well as by $H_2O_2$—yielding peracid salts, e.g. caroates ($KHSO_5$), perbenzoates or peroxyphthalates. It is advisable to incorporate the usual water-soluble and/or water-insoluble stabilizers for the peroxy compounds together with the latter in amounts of 0.25% to 10% by weight. The water-insoluble bleach stabilizers, which amount to 1% to 8% by weight, preferably 2% to 7% by weight of the total preparation, are preferably the magnesium silicates $MgO:SiO_2=4.1$ to 1:4, preferably 2:1 to 1:2 and more particularly 1:1 usually obtained by precipitation from aqueous solutions. In their place other alkaline earth metal or tin silicates of corresponding composition are usable. Water-containing oxides of tin are also suitable as bleach stabilizers. Water-soluble stabilizers, which may be present together with water-insoluble ones, are the organic heavy metal complex formers, which are employed in amounts of 0.25% to 5%, preferably 0.5% to 2.5%, of the weight of the total preparation.

To obtain a satisfactory bleaching action when washing at temperatures below 80° C., in particular in the range of 20° C. to 60° C., preferably activator-containing bleaching components are incorporated into the preparations. The bleach activators usable according to the invention include, in particular, the N-diacylated and N,N'-tetraacylated amines, for example N,N,N',N'-tetraacetyl-methylenediamine or N,N,N',N'-tetraacetyl-ethylenediamine, N,N-diacetylaniline and N,N-diacetyl-p-toluidine or 1,3-diacylated hydantoins, for example, 1,3-diacetyl-5,5-dimethyl hydantoin and 1,3-dipropionyl hydantoin, as well as the acylated glycoluril compounds such as tetra-acetylglycoluril and tetra-propionyl-glycoluril.

The detergents may contain optical brighteners such as those for cotton, in particular, derivatives of diaminostilbene-disulfonic acid or their alkali metal salts. Suitable, for example, are the salts of 4,4'-bis (2-anilino-4-morpholino-1,3,5-triazine-6-yl-amino)-stilbene-2,2'-disulfonic acid or similarly constructed compounds which carry instead of the morpholino group a diethanolamino group, a methylamino group or a 2-methoxyethylamino group. Also optical brighteners for polyamide fibers can be employed such as those of the type of the 1,3-diaryl-2-pyrazolines, for example, 1-(p-sulfamoylphenyl)-3-(p-chlorophenyl)-2-pyrazoline as well as similarly constructed compounds which carry instead of the sulfamoyl group, the methoxycarbonyl, 2-methoxy-ethoxycarbonyl, acetylamino or vinylsulfonyl groups. Useful polyamide brighteners are, further, the substituted amino coumarins, for example, 4-methyl-7-dimethylamino-coumarin or 4-methyl-7-diethylamino coumarin. There may also be used as polyamide brighteners the compounds 1-(2-benzimidazolyl)-2-(1-hydroxyethyl-2-benzimidazolyl)-ethylene and 1-ethyl-3-phenyl-7-diethylamino-carbostyril. Also optical brighteners for polyester and polyamide fibers can be employed, such as 2,5-di-(2-benzoxazolyl)-thiophene, 2-(2-benzoxazolyl)-naphtho [2,3-b]-thiophene and 1,2-di-(5-methyl-2-benzoxazolyl)-ethylene. Further, brighteners of the type of the substituted 4,4'-distyryl-diphenyl may be present, for example, 4,4'-bis(4-chloro-3-sulfostyryl)-diphenyl. Mixtures of the aforesaid brighteners may also be used.

Water-soluble organic solvents are employed as liquid carriers. Above all the lower alcohols, ether alcohols and glycols with 1 to 6 carbon atoms are suitable such as alkanols having 1 to 6 carbon atoms, alkanediols having 2 to 6 carbon atoms, alkoxyalkanols having 3 to 6 carbon atoms and alkoxyalkoxyalkanols having 4 to 6 carbon atoms, for example, methanol, ethanol, propanol, isopropyl alcohol, ethylene glycol, propylene glycol, diethylene glycol, methyl ethylene glycol, ethyl ethylene glycol, butyl ethylene glycol, etc.

The following examples are illustrative of the invention without being limitative in any manner.

EXAMPLES

The following examples describe the production of the compounds of formula I of the invention, their use as antimicrobial substances as well as their use as constituents of surface-active combinations in detergents which are especially suitable for cold temperature washing.

EXAMPLE 1

There is given first a general procedure for the manufacture of the substances of formula I of the invention. In analogy thereto the substances of formula I listed in Table I below were manufactured.

A mixture of ε-caprolactam and the vicinal hydroxyalkylamine of formula II in the stated molar ratios was heated to 230° C. to 250° C. while agitating vigorously and flushing with dried nitrogen. The mixture was then left at this temperature for 3 to 20 hours. After termination of the reaction, the resulting water-clear, thin melt was cooled. In the case of further reaction with ethylene oxide, the melt was transferred to an autoclave, at a temperature of 150° C., and admixed with the stated amount of ethylene oxide at a temperature of 100°–130° C. Agitation was continued at this temperature for 2–3 hours, and then the reaction mixture was cooled.

TABLE 1

| Compound No. | Reaction Products of Formula I (i = non-terminal) (α = terminal, $R_2$ = H) $R_1-CH-CH-R_2$ | $R_3$ | Mols ε-Caprolactam x | Mols EO y | Constants $n_D^{50}$ (Refractive index at 50° C. in glacial acetic acid; quantity ratio 1:1) |
|---|---|---|---|---|---|
| 1 | α-$C_{12}$/$C_{14}$-Alkylene | —$CH_2$—$CH_2$—$CH_2$—$NH_2$ | 2 | 0 | 1.4530 |
| 2 | " | " | 3 | 0 | 1.4485 |

TABLE 1-continued

| Compound No. | Reaction Products of Formula I (i = non-terminal) (α = terminal, R₂ = H) $R_1-CH-CH-R_2$ | $R_3$ | Mols ε-Caprolactam x | Mols EO y | Constants $n_D^{50}$ (Refractive index at 50° C. in glacial acetic acid; quantity ratio 1:1) |
|---|---|---|---|---|---|
| 3 | " | " | 2 | 1 | 1.4400 |
| 4 | " | " | 2 | 3 | Mp 130–150° C. |
| 5 | " | $-CH_2-CH_2-NH_2$ | 2 | 0 | 1.4452 |
| 6 | " | " | 2 | 1 | 1.4485 |
| 7 | " | " | 2 | 2 | 1.4440 |
| 8 | " | " | 2 | 3 | 1.4602 |
| 9 | " | $-CH_3$ | 2 | 0 | 1.4370 |
| 10 | " | " | 2 | 1 | Mp 150–157° C. |
| 11 | " | " | 3 | 0 | Mp ca. 200° C. |
| 12 | " | $-(CH_2)_6-NH_2$ | 2 | 0 | 1.4420 |
| 13 | " | " | 2 | 1 | 1.4450 |
| 14 | " | " | 3 | 0 | 1.4491 |
| 15 | " | " | 2 | 3 | 1.4446 |
| 16 | α-$C_{14}$/$C_{16}$-Alkylene | $-CH_2-CH_2-NH_2$ | 2 | 0 | 1.4470 |
| 17 | " | " | 2 | 1 | 1.4461 |
| 18 | " | " | 2 | 2 | 1.4460 |
| 19 | " | " | 2 | 3 | 1.4457 |
| 20 | " | $-CH_2-CH_2-CH_2-NH_2$ | 2 | 0 | 1.4418 |
| 21 | " | " | 2 | 1 | 1.4460 |
| 22 | " | " | 2 | 2 | 1.4470 |
| 23 | " | " | 2 | 3 | 1.4432 |
| 24 | α-$C_{16}$/$C_{18}$-Alkylene | $-CH_2-CH_2-NH_2$ | 2 | 0 | 1.4413 |
| 25 | " | " | 2 | 1 | 1.4453 |
| 26 | " | " | 2 | 2 | 1.4483 |
| 27 | " | " | 2 | 3 | 1.4446 |
| 28 | " | $-CH_2-CH_2-CH_2-NH_2$ | 2 | 0 | 1.4430 |
| 29 | " | " | 2 | 1 | 1.4423 |
| 30 | " | " | 2 | 2 | 1.4473 |
| 31 | " | " | 2 | 3 | 1.4501 |
| 32 | i-$C_{11}$-$C_{14}$-Alkylene | $-CH_2-CH_2-NH_2$ | 2 | 0 | 1,4526 |
| 33 | " | " | 2 | 1 | 1,4522 |
| 34 | " | " | 2 | 2 | 1,4452 |
| 35 | " | " | 2 | 3 | 1,4518 |
| 36 | " | $-CH_2-CH_2-CH_2-NH_2$ | 2 | 0 | 1,4539 |
| 37 | " | " | 2 | 1 | 1,4521 |
| 38 | " | " | 2 | 2 | 1,4528 |
| 39 | " | " | 2 | 3 | 1,4508 |
| 40 | " | $-CH_2-CH_2-CH_2-N(CH_3)_2$ | 2 | 0 | Mp ca. 130° C. |
| 41 | " | " | 2 | 1 | Mp 120–140° C. |
| 42 | " | " | 2 | 2 | 1,4420 |
| 43 | " | " | 2 | 3 | 1,4332 |
| 44 | i-$C_{15}$-$C_{18}$-Alkylene | $-CH_2-CH_2-CH_2-NH_2$ | 2 | 0 | 1,4480 |
| 45 | " | $-CH_3$ | 2 | 0 | Mp 150–170° C. |
| 46 | " | " | 2 | 1 | 1,4279 |
| 47 | " | " | 3 | 0 | Mp 220–230° C. |
| 48 | " | $-H$ | 2 | 0 | 1,4398 |
| 49 | " | " | 2 | 1 | 1,4360 |
| 50 | " | " | 3 | 0 | 1,4430 |
| 51 | " | $-CH_2-CH_2-NH_2$ | 2 | 0 | 1,4518 |
| 52 | " | " | 2 | 1 | 1,4488 |
| 53 | " | " | 2 | 2 | 1,4511 |
| 54 | " | " | 2 | 3 | 1,4519 |
| 55 | α-$C_{15}$-$C_{18}$-Alkylene | $-CH_2-CH_2-CH_2-NH_2$ | 2 | 0 | 1,4430 |
| 56 | " | " | 2 | 1 | 1,4451 |
| 57 | " | " | 3 | 0 | 1,4432 |
| 58 | " | " | 2 | 3 | 1,4426 |
| 59 | " | $-CH_3$ | 2 | 0 | 1,4405 |
| 60 | " | " | 2 | 1 | 1,4392 |
| 61 | " | " | 3 | 0 | 1,4359 |

EXAMPLE 2

25 parts by weight of glacial acetic acid were stirred into 100 parts by weight of a melt at 80° C. of the compounds listed in Table 1, so that the temperature did not exceed 100° C. After the entire acetic acid had been added, 275 parts of fully deionized water were added. The pale yellow solution thus obtained served as stock solution for incorporation into a variety of products.

EXAMPLE 3

To determine the antimicrobial activity of the reaction products, their minimum inhibiting concentration on the bacteria and fungi listed below was determined.
(1) *Staphylococcus aureus* (*S. aureus*)
(2) *Escherichia coli* (*E. coli*)
(3) *Pseudomonas aeruginosa* (*Ps. aeruginosa*)
(4) *Candida albicans* (*C. albicans*).

The minimum inhibiting concentration of the products to be tested was determined by means of the dilution test according to the guidelines for the testing of chemical disinfectants, published by Deutsche Gesellschaft für Hygiene und Mikrobiologie (1959). The tests were carried out in test tubes filled with Standard-I-Bouillon (Merck) or with beer wort (8° Bé) in a dilution of 1:5 with distilled water. After addition of the active substances, the volume of nutrient solution in the test tubes was 10 ml. Then the tubes were seeded with 0.1 ml of test germ suspensions. The seeded tubes were incubated in the incubator 3 days at 37° C. for bacteria and 6 days at 30° C. for fungi. Then it was determined which substance concentration added to the culture medium was just sufficient to completely suppress growth of the germs. The value thus determined was referred to as inhibiting concentration (m.i.c.). The tests were carried out in the concentration intervals 1000 ppm, 500 ppm, 250 ppm, 100 ppm, 50 ppm, 25 ppm and 10 ppm.

In this dilution test, the inhibiting concentrations listed in Table 2 below were determined for the individual products with the above-named bacteria. The reaction products are characterized by their alkyl radicals, the ratio of hydroxyalkylamine to ε-caprolactam, and the number of mols of ethylene oxide per mol of hydroxyalkylamine.

Table 2

Microbistatic effect in the tube test
Numbers: Inhibiting concentrations in ppm $R_1$—CH—CH—$R_2$ + n Caprolactam + x EO
|   |   OH   NH—$R_3$

| | n= | x= | S. aureus | E. coli | Ps.aerug. | C. albicans |
|---|---|---|---|---|---|---|
| $R_1$=$C_{12}H_{25}$—$C_{14}H_{29}$ | 2 | 0 | <10 | 50 | 100 | 100 |
| $R_3$=—$(CH_2)_2$—$NH_2$ | 2 | 1 | <10 | 50 | 250 | 100 |
| (a) $R_2$=—H | 2 | 2 | <10 | 100 | 500 | 100 |
| | 2 | 3 | <10 | 250 | 500 | 100 |
| $R_1$=$C_{14}H_{29}$—$C_{16}H_{33}$ | 2 | 0 | <10 | 50 | 100 | 100 |
| $R_3$=—$(CH_2)_3$—$NH_2$ | 2 | 1 | <10 | 100 | 250 | 100 |
| (b) | | | | | | |
| $R_2$=—H | 2 | 2 | <10 | 500 | >1000 | 250 |
| | 2 | 3 | 100 | >1000 | >1000 | 100 |
| $R_1$=$C_{10}H_{21}$—$C_{12}H_{25}$ | 2 | 0 | 25 | 25 | 500 | 250 |
| $R_3$=—$CH_3$ | 3 | 0 | 50 | 250 | 1000 | 250 |
| (c) | | | | | | |
| $R_2$=—H | 2 | 1 | 50 | 250 | 1000 | 250 |
| $R_1$=$C_{10}H_{21}$—$C_{12}H_{25}$ | 2 | 0 | 10 | 25 | 25 | 50 |
| $R_3$=—$(CH_2)_6$—$NH_2$ | 2 | 1 | 10 | 50 | 100 | 250 |
| (d) | | | | | | |
| $R_2$=—H | 3 | 0 | 25 | 50 | 100 | 100 |
| | 2 | 3 | <10 | 50 | 500 | 100 |
| $R_1$ + $R_2$=$C_9H_{20}$—$C_{11}H_{24}$ | 2 | 0 | 100 | 250 | 1000 | 1000 |
| $R_3$=—$(CH_2)_3$—$N(CH_3)_2$ | 2 | 1 | 50 | 250 | 500 | 1000 |
| (e) | 2 | 2 | 50 | 250 | 500 | 1000 |
| | 2 | 3 | 50 | 100 | 500 | 1000 |
| $R_1$ + $R_2$=$C_{13}H_{28}$—$C_{16}H_{34}$ | 2 | 0 | 25 | 500 | >1000 | 500 |
| (f) $R_3$=—$CH_3$ | 2 | 1 | 25 | 100 | >1000 | 100 |
| | 3 | 0 | 25 | >1000 | >1000 | 500 |
| $R_1$ + $R_2$=$C_{13}H_{28}$—$C_{16}H_{34}$ | 2 | 0 | 50 | 100 | >1000 | 500 |
| (g) $R_3$=—H | 2 | 1 | 25 | 500 | >1000 | 500 |
| | 3 | 0 | 25 | 100 | >1000 | 100 |

The strong inhibiting effect of the reaction products of the invention on bacteria and fungi can be seen convincingly from Table 2.

EXAMPLE 4

The microbicidal effect of some reaction products of the invention was determined by means of the suspension test. The method of this test procedure is taken from the guide-lines for the testing of chemical disinfectants, published by Deutsche Gesellschaft fur Hygiene und Mikrobiologie (1959). According to these guide-lines, 0.1 ml germ suspension of the bacteria and fungi listed below was pipetted into test tubes at a temperture of 18° to 21° C:

(1) Staphylococcus aureus (S. aureus)
(2) Escherichia coli (E. coli)
(3) Pseudomonas aeruginosa (Ps. aeruginosa)
(4) Candida albicans (C. albicans).

To these germ suspensions, 10 ml of the various dilution amounts of the reaction products of the invention to be tested were placed in distilled water. The concentrations of the products of the invention were 100 ppm, 250 ppm and 500 ppm. After contact times of 1, 2.5, 5, 10, 20, 30 and 60 minutes, one platinum-wire loop amount of material was taken from each of the test tubes and innoculated into 10 ml of nutrient solution which contained 3% Tween 80 and and 0.3% lecithin as de-inhibitor. The nutrient solutions innoculated with bacteria were incubated at 37° C., those innoculated with fungi at 30° C. After six days the cultures were examined macroscopically for growth and in this way the times required for a complete kill at the various concentrations were determined, which are compiled in the following Table 3.

Table 3

Microbicidal action in the suspension test (Tween-lecithin, dist. water, RT)
Numbers: Killing time in minutes

| $R_1$—CH—CH—$R_2$ + n Caprolactam + x EO<br>　　\|　　\|<br>　　OH　NH—$R_3$ | n= | x= | Conc. (ppm) | S. aureus | E. coli | Ps. aerug. | C. albic. | Examined at pH |
|---|---|---|---|---|---|---|---|---|
| (a) $R_1=C_{12}H_{25}$—$C_{14}H_{29}$<br>$R_3=$—$(CH_2)_2$—$NH_2$<br>$R_2=H$ | 2 | 0 | 500<br>250<br>100 | 10<br>20<br>60 | 10<br>20<br>60 | 10<br>20<br>60 | 10<br>20<br>40 | 8.5 |
| | 2 | 1 | 500<br>250<br>100 | 2.5<br>10<br>20 | 40<br>120<br>120 | 60<br>>120<br>>120 | 2.5<br>10<br>40 | 8.8 |
| (b) $R_1=C_{14}H_{29}$—$C_{16}H_{33}$<br>$R_3=$—$(CH_2)_3$—$NH_2$<br>$R_2=H$ | 2 | 0 | 500<br>250<br>100 | 2.5<br>5<br>10 | 40<br>40<br>>120 | 60<br>60<br>>120 | 10<br>10<br>60 | 8.6 |
| | 2 | 1 | 1000<br>500<br>250<br>100 | <br>5<br>5<br>10 | <br>40<br>60<br>60 | 120<br>120<br>>120<br>120 | <br>10<br>10<br>120 | 8.5 |
| (c) $R_1=C_{10}H_{21}$—$C_{12}H_{25}$<br>$R_3=$—$CH_3$<br>$R_2=$—H | 2 | 0 | 1000<br>500<br>250<br>100<br>50 | <br>40<br>40<br>>120<br>>120 | <br>10<br>120<br>>120<br>>120 | 2.5<br>5<br>20<br> <br>  | 2.5<br>10<br>40<br> <br>  | 7.1 |
| (d) $R_1=C_{10}H_{21}$—$C_{12}$—$H_{25}$<br>$R_3=$—$(CH_2)_6$—$NH_2$<br>$R_2=$—H | 2 | 0 | 500<br>250<br>100<br>50 | 5<br>5<br>20<br>>120 | 5<br>40<br>>120<br>>120 | 2.5<br>20<br>60<br>120 | >120<br>>120<br>>120<br>>120 | 7.2 |
| | 2 | 1 | 500<br>250<br>100<br>50 | 10<br>10<br>60<br>>120 | 5<br>40<br>>120<br>>120 | 2.5<br>5<br>>120<br>>120 | >120<br>>120<br>>120<br>>120 | 7.2 |
| | 2 | 3 | 1000<br>500<br>250<br>100 | <br>5<br>5<br>20 | <br>40<br>40<br>120 | 60<br>120<br>>120<br>  | <br>10<br>10<br>20 | 8.9 |
| (e) $R_1 + R_2=C_9H_{20}$—$C_{11}H_{24}$<br>$R_3=$—$(CH_2)_2$—$NH_2$ | 2 | 0 | 500<br>250<br>100 | 5<br>5<br>5 | 60<br>120<br>>120 | 40<br>120<br>>120 | 10<br>20<br>120 | 8.8 |
| | 2 | 1 | 1000<br>500<br>250<br>100 | —<br>10<br>20<br>120 | —<br>60<br>60<br>>120 | 20<br>60<br>>120<br>— | —<br>40<br>60<br>120 | 8.8 |
| | 2 | 2 | 1000<br>500<br>250<br>100 | —<br>2.5<br>5<br>5 | —<br>40<br>>120<br>>120 | 120<br>>120<br>>120<br>— | —<br>10<br>40<br>40 | 8.7 |
| | 2 | 3 | 1000<br>500<br>250 | <br>2.5<br>2.5 | 40<br>40<br>60 | >120<br>>120<br>>120 | 10<br>20<br>60 | 8.7 |
| (f) $R_1 + R_2=C_{13}H_{28}$—$C_{16}H_{34}$<br>$R_3=H$ | 2 | 0 | 2500<br>1000<br>500<br>250<br>100<br>50 | —<br>—<br>5<br>5<br>10<br>40 | —<br>—<br>2.5<br>10<br>60<br>120 | 2.5<br>5<br>20<br>—<br>—<br>— | —<br>—<br>20<br>40<br>40<br>120 | 7.2 |

The above table illustrates clearly the very good killing activity of the reaction products of the invention on bacteria and fungi.

EXAMPLE 5

The cooling system of a steam power plant of a volume of 6000 m³, an hourly feed of 150 m³ and a circulation of 11,000 m³/h with about triple concentration was treated during a period of 6 months with a mixture of 1-hydroxyethane-1,1-diphosphonic acid and aminotrimethylene phosphonic acid (weight ratio 1:1). The quantity of the mixture added was 4 gm/m³. Despite good protection against corrosion and scale, disturbances occurred again and again due to growth of slime-forming bacteria on the condenser.

For this reason there was added an amount of 5 gm/m³ of a reaction product of 1 mol of ethylene oxide to 1 mol of a reaction product of a hydroxyalkylamine of the claimed general formula, wherein $R_1 = C_{14}H_{29}$—$C_{16}H_{33}$, $R_3 =$ —$(CH_2)_3$ $NH_2$, $R_2 = H$, and ε-caprolactam in the molar ratio 1:2. By this combined addition of reaction product of the invention and phosphonic acids, the disturbances in the cooling system could be eliminated completely. No increase of germ growth in the cooling water was observed.

EXAMPLE 6

A number of antimicrobial washing and cleaning agent formulations for commercial use are given below. Explanations for the various additions are given later on, before Examples 9 to 17.

6(a) Prewashing agent with simultaneous antimicrobial action 8.0 parts by weight olefin sulfonate
4.0 parts by weight soap
0.3 parts by weight foam inhibitor (stearone)
36.0 parts by weight $Na_4P_2O_7$ -continued

| | | |
|---|---|---|
| | 7.5 | parts by weight NaOH |
| | 10.2 | parts by weight Na$_2$SO$_4$ |
| | 4.0 | parts by weight reaction product of formula I. |
| 6(b) | Antimicrobial cleaning agent for laundries | |
| | 25 | parts by weight hydrogenated tallow fatty alcohol sulfate |
| | 35 | parts by weight Na$_5$P$_3$O$_{10}$ |
| | 7 | parts by weight Na$_2$CO$_3$ |
| | 15 | parts by weight Na$_2$SO$_4$ |
| | 5 | parts by weight Na$_2$O . 3.3 SiO$_2$ |
| | 1 | part by weight carboxymethyl-cellulose |
| | 2 | parts by weight reaction product of formula I |
| | 10 | parts by weight pentasodium amino-tri-(methylene phosphate). |
| 6(c) | Antimicrobial acid cleaning agent for the beverage industry | |
| | 50 | parts by weight phosphoric acid (80%) |
| | 4 | parts by weight nonylphenol + 9 EO |
| | 5 | parts by weight 1-hydroxyethane-1,1-diphosphonic acid |
| | 1 | part by weight reaction product of formula I |
| | 40 | parts by weight water. |
| 6(d) | Antimicrobial delicate detergent | |
| | 30 | parts by weight dodecylbenzene sulfonate |
| | 2 | parts by weight toluene sulfonate |
| | 8 | parts by weight sodium coconut-fatty alcohol sulfate |
| | 30 | parts by weight sodium sulfate |
| | 1 | part by weight sodium carboxymethyl-cellulose |
| | 4 | parts by weight reaction product of formula I |
| | 25 | parts by weight water. |

Any one of the reaction products of the invention of formula I, as listed in Table 1, can be employed in the above recipes.

The reaction products of the invention can find further application as antimicrobial substances in dry cleaning solutions based on organic solvents with a low water content. Here the substances are added to the cleaning solutions in a concentration of 1 to 10 gm/l. The cleaning intensifiers on a base of anionic-active and nonionic interface-active compounds are normally added to the cleaning solutions in the form of concentrates which contain, in addition to the interface-active compound, such solvents as chlorinated hydrocarbons or mineral oil, also possibly solubilizers, e.g., isopropanol, and water. The reaction products of the invention can be incorporated into these concentrates and proportioned together with the cleaning intensifier.

In dry cleaning, enough water is added to the cleaning solutions that during the cleaning process the relative humidity in the steam zone above the solution is at least 70%.

Besides their use in cleaning agents for obtaining an antimicrobial activity of the product, the substances of the invention can be used for the preservation of cosmetics, starch pastes, glues, dispersion dyes, cutting and drilling oils and the like.

For this purpose, an addition of 0.1% to 2% by weight, based on the product to be preserved, is generally sufficient.

EXAMPLE 7

A major area of use of the reaction products of the invention is the preservation of industrial and utility water. An additive suitable for this purpose has the following composition:

300 parts by weight stock solution of the acetate of Compound No. 17 in Table 1 according to Example 2.
15 parts by weight of the sodium salt of 1-hydroxyethane-1,1-diphosphonic acid
15 parts by weight of the sodium salt of amino-tri-(methylene phosphonic acid)

bring to 1000 parts by weight with fully deionized water.

100 cc of this solution/m$^3$ of the industrial water to be preserved, for example, cooling water for cooling towers, are used.

EXAMPLE 8

This example describes the composition of a low-foam cold water detergent, which is suitable in particular for machine washing. The active substances were the compounds of formula I according to Table 1.

| % by Weight | |
|---|---|
| 6.0 | sodium dodecylbenzene sulfonate |
| 1.0 | adduct from 1 mol of tallow fatty alcohol and 14 mols of ethylene oxide |
| 1.0 | adduct from 1 mole of oleyl/cetyl alcohol and 5 mols of ethylene oxide |
| 2.5 | reaction product of formula I |
| 3.0 | soap (Na-salt of essentially C$_{18}$–C$_{22}$ fatty acids) |
| 60.0 | sodium tripolyphosphate |
| 2.0 | waterglass (Na$_2$O + 3.35 SiO$_2$) |
| 0.2 | sodium ethylenediaminetetraacetate |
| 1.2 | carboxymethyl-cellulose, sodium salt |
| balance | sodium sulfate and water. |

To establish the cold washing capacity, Launderometer ® tests were carried out under the following conditions:

Washing temperature 20° C.; water hardness 16° dH; detergent concentration 4.0 gm/l; bath ratio 1:30 with finished cotton and polyester/cotton fabric; washing time 30 minutes. The comparison was with a detergent which contained, instead of the reaction product of formula I, 2.5% by weight of either sodium sulfate of oleyl/cetyl alcohol + 5 EO. From the following numerical values of the brightening degree (% remission) measured on the test fabrics, the marked improvement of the washing power when using the detergent of the invention is clearly evident.

Table 4

| | | % Remission | |
|---|---|---|---|
| | Detergent per Example 8 | Finished Cotton | Polyester/ Finished Cotton |
| 8(a) | with 2.5% active Compound No. 13 (Table 1) | 61.6 | 63.4 |
| 8(b) | with 2.5% oleyl/cetyl alcohol + 5 EO | 57.1 | 50.5 |
| 8(c) | with 2.5% sodium sulfate | 56.3 | 50.5 |

EXAMPLES 9 to 17

There follows now Table 5 with further examples of washing and cleaning agents according to the invention. The salt type of these agents named in the examples, such as the salt type of tensides, other organic salts, as well as inorganic salts, are present as sodium salts unless otherwise expressly stated. The designations or abbreviations in the examples have the following meaning:

"ABS"—the salt of an alkylbenzene sulfonic acid obtained by condensation of straight-chain olefins with benzene and sulfonation of the alkyl benzene thus formed, with 10 to 15, essentially 11 to 13, carbon atoms in the alkyl chain;

"Olefin sulfonate"—a mixture of hydroxyalkane sulfonates, alkene sulfonates and alkane di-sulfonates obtained by sulfonation of α-olefins with 12 to 18 carbon atoms with $SO_3$ and hydrolysis of the sulfonation product with sodium hydroxide;

"Fs-ester sulfonate"—a sulfonate obtained from hydrogenated palm kernel fatty acid methyl ester through sulfonation with $SO_3$;

"Alkane sulfonate"—a sulfonate obtained by the sulfoxydation of a $C_{12-18}$ paraffin;

"Soap"—a soap prepared from a hardened mixture of equal parts by weight of tallow and rapeseed oil fatty acids (iodine number = 1);

"TA+x EO"—the addition products of ethylene oxide (EO) to hardened tallow fatty alcohol (TA) (iodine number = 0.5), the numerical data for x designating the molar quantity of ethylene oxide added to 1 mol of alcohol;

"Bleach activator"—the compound tetraacetylglycoluril;

"Perborate"—a technical product of the approximate composition $NaBO_2.H_2O_2.3H_2O$;

"EDTA"—the salt of ethylenediaminetetraacetic acid;

"NTA"—the salt of nitrilotriacetic acid;

"CMC"—the salt of carboxymethyl-cellulose.

The examples of the following Table 5 involve, in the case of Examples 9, 10, 16 and 17, phosphate-containing detergent powders with bleaching action, in Examples 11 and 12, prewash and main cycle detergent powders without bleaching action, while Examples 13 to 15 represent a fine detergent in powder form, a liquid detergent, and a phosphate-free detergent powder, respectively.

If, in the examples of Table 5, the active substances used there are replaced by other reaction products of formula I, in particular the compounds of Table 1, comparable results will be obtained. This is the case also if, for example, in the formulations of Examples 9, 13 and 16, one-half of the component of 40% by weight sodium tripolyphosphate is replaced by a crystalline aluminosilicate, for example, of the composition $0.96 Na_2O.1 Al_2O_3.1.96SiO_2.4H_2O$, means particle size $5.4\mu$, calcium binding power, 172 mg CaO/gm.

Table 5

| Constituents | Detergent Constituents in % for Examples | | | | | | | | |
|---|---|---|---|---|---|---|---|---|---|
| | 9 | 10 | 11 | 12 | 13 | 14 | 15 | 16 | 17 |
| ABS | 6.0 | — | — | — | 6.5 | — | 6.0 | 6.0 | — |
| TA + 14 EO | 1.0 | — | 1.0 | 1.5 | — | 4.0 | 1.0 | 2.5 | 4.0 |
| TA + 5EO | 1.0 | 1.5 | 1.0 | — | — | — | 1.0 | 1.5 | 4.0 |
| Fs-ester sulfonate | — | — | 3.0 | 6.0 | — | — | — | — | — |
| Alkane sulfonate | — | — | — | — | — | 8.0 | — | — | — |
| Olefin sulfonate | — | 6.0 | 3.0 | — | — | — | — | — | — |
| Tallow alcohol-3EO-sulfate | — | — | — | — | 4.0 | — | — | — | — |
| Soap | 3.5 | 3.5 | 2.5 | 3.0 | 0.5 | — | 3.0 | 3.0 | 3.0 |
| Potassium toluene sulfonate | — | — | — | — | — | 4.0 | — | — | — |
| Active Compound No. 13 | 2.5 | — | — | 1.5 | 1.5 | — | — | 1.5 | 1.0 |
| Active Compound No. 12 | — | — | 1.0 | — | — | 1.8 | — | — | — |
| Active Compound No. 15 | — | 1.0 | — | — | — | — | 1.5 | — | — |
| $Na_5P_3O_{10}$ | 40.0 | 30.0 | 60.0 | 55.0 | 40.0 | — | — | 40.0 | 35.0 |
| NTA | — | 5.0 | — | 5.0 | — | — | — | — | — |
| $K_4P_2O_7$ | — | — | — | — | — | 10.0 | — | — | — |
| EDTA | 0.2 | 0.2 | — | — | — | — | 0.2 | 0.2 | 0.2 |
| Perborate | 15.0 | 15.0 | — | — | — | — | 20.0 | 25.0 | 15.0 |
| Bleach activator | 15.0 | 15.0 | — | — | — | — | — | — | 15.0 |
| Water glass | 3.0 | 3.0 | 4.0 | 5.0 | 3.5 | — | 15.0 | 3.0 | 5.0 |
| Sodium carbonate | — | — | 3.0 | 3.0 | — | — | 6.0 | — | — |
| Mg silicate | 2.0 | 2.0 | — | — | — | — | 2.0 | 2.0 | 2.0 |
| CMC | 1.5 | 1.8 | 1.5 | 1.4 | — | — | 1.2 | 1.5 | 1.5 |
| Isopropyl alcohol | — | — | — | — | — | 5.0 | — | — | — |
| Balance: Na sulfate, enzymes, opt. brightener, perfume, water | | | | | | Balance Water | | | |

The preceding specific embodiments are illustrative of the practice of the invention. It is to be understood, however, that other expedients known to those skilled in the art or disclosed herein, may be employed without departing from the spirit of the invention or the scope of the appended claims.

We claim:

1. Reaction products of ε-caprolactam with vicinal hydroxyalkylamines which are derived from terminal mono-olefins or mixtures of mono-olefins with statistically distributed non-terminal double bonds and possible adducts thereof with epoxyalkanes having the overall formula

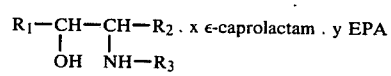

wherein $R_1$ and $R_2$ are members selected from the group consisting of hydrogen and alkyl having 1 to 16 carbon atoms with the proviso that the sum of the carbon atoms in $R_1$ and $R_2$ is from 8 to 16 when $R_1$ and $R_2$ are alkyl and from 8 to 16 when $R_1$ or $R_2$ is hydrogen, $R_3$ is a member selected from the group consisting of hydrogen, alkyl having 1 to 5 carbon atoms and

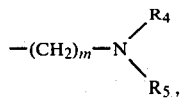

where m is an integer from 2 to 10, and $R_4$ and $R_5$ are members selected from the group consisting of hydrogen and alkyl having 1 to 3 carbon atoms, EPA is an epoxide selected from the group consisting of ethylene oxide, propylene oxide and glycide, x is a member representing mols of from 1.5 to 3.5 and y is a number representing mols of from 0 to 5; and the organic and inorganic acid salts thereof.

2. The reaction product of claim 1 wherein $R_1$ and $R_2$ are alkyl.

3. The reaction product of claim 1 wherein one of $R_1$ or $R_2$ is hydrogen.

4. The reaction product of claim 1 wherein $R_3$ is

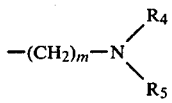

and m is an integer from 2 to 6.

5. The reaction product of claim 4 wherein $R_4$ and $R_5$ are methyl.

6. the reaction product of claim 1 wherein x has a value of between 2 and 3.

7. Reaction products of ε-caprolactam with vincinal hydroxyalkylamines which are derived from terminal mono-olefins or mixtures of mono-olefins with statistically distributed non-terminal double bonds having the overall formula:

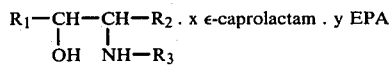

wherein $R_1$ and $R_2$ are members selected from the group consisting of hydrogen and alkyl having 1 to 16 carbon atoms with the proviso that the sum of the carbon atoms in $R_1$ and $R_2$ is from 8 to 16 when $R_1$ and $R_2$ are alkyl and from 8 to 16 when $R_1$ or $R_2$ is hydrogen, $R_3$ is a member selected from the group consisting of hydrogen, alkyl having 1 to 5 carbon atoms and

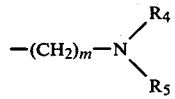

where m is an integer from 2 to 10, and $R_4$ and $R_5$ are members selected from the group consisting of hydrogen and alkyl having 1 to 3 carbon atoms, and x is a number representing mols of from 1.5 to 3.5, and the organic and inorganic acids salts thereof.

8. Reaction products of ε-caprolactam with vicinal hydroxylakylamines which are derived from terminal mono-olefins or mixtures of mono-olefins with statistically distributed nonterminal double bonds adducted with epoxy alkanes having the overall formula:

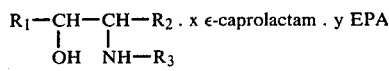

wherein $R_1$ and $R_2$ are members selected from the group consisting of hydrogen and alkyl having 1 to 16 carbon atoms with the proviso that the sum of the carbon atoms in $R_1$ and $R_2$ is from 8 to 16 when $R_1$ and $R_2$ are alkyl and from 8 to 16 when $R_1$ or $R_2$ is hydrogen, $R_3$ is member selected from the group consisting of hydrogen, alkyl having 1 to 5 carbon atoms and

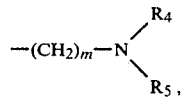

when m is an integer from 2 to 10, and $R_4$ and $R_5$ are members selected from the group consisting of hydrogen and alkyl having 1 to 3 carbon atoms, EPA is an epoxide selected from the group consisting of ethylene oxide, propylene oxide and glycide, x is a number representing mols of from 1.5 to 3.5 and y is a number representing mols of from 0.5 to 5; and the organic and inorganic acid salts thereof.

9. The reaction product of claim 1 wherein EPA is ethylene oxide.

10. The reaction product of claim 8 wherein EPA is ethylene oxide and y has a value of between 1 and 3.

11. The process for the production of the reaction product of claim 1 comprising reacting 1 mol of a vicinal hydroxyalkylamine of the formula

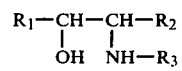

wherein $R_1$, $R_2$ and $R_3$ have the values given in claim 1, with 1 to 5 mols of ε-caprolactam at a temperature of from 180° C. to 250° C. for 3 to 20 hours, optionally further reacting the product with 0 to 5 mols of EPA, wherein EPA has the meaning given in claim 1, at a temperature of from 50° C. to 150° C., and recovering said reaction product.

12. A process for the prevention of the growth of microorganisms selected from the group consisting of gram-positive bacteria, gram-negative bacteria, fungi and algae in an aqueous environment, which consists essentially of contacting said microorganisms with an amount effective to prevent the growth of said microorganisms of a reaction product of ε-caprolactam with vicinal hydroxyalkamines which are derived from terminal mono-olefins or mixtures of mono-olefins with statistically distributed nonterminal double bonds and possible adducts thereof with epoxyalkanes having the overall formula:

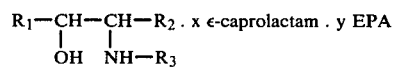

wherein $R_1$ and $R_2$ are members selected from the group consisting of hydrogen and alkyl having 1 to 16 carbon atoms with the proviso that the sum of the carbon atoms in $R_1$ and $R_2$ is from 8 to 16 when $R_1$ and $R_2$ are alkyl and from 8 to 16 when $R_1$ or $R_2$ is hydrogen, $R_3$ is a member selected from the group consisting of hydrogen, alkyl having 1 to 5 carbon atoms and

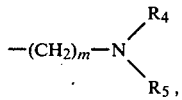

where m is an integer from 2 to 10, and $R_4$ and $R_5$ are members selected from the group consisting of hydrogen and alkyl having 1 to 3 carbon atoms, EPA is an epoxide selected from the group consisting of ethylene oxide, propylene oxide and glycide, x is a number representing mols of from 1.5 to 3.5 and y is a number representing mols of from 0 to 5; and the organic and inorganic acid salts thereof.

13. The process of claim 12 wherein said reaction product is in combination with an organic phosphonic acid complex-former in a weight ratio of 1:10 to 10:1.

14. The process of claim 13 wherein said weight ratio is from 3:1 to 1:3.

15. The process of claim 13 wherein said aqueous environment is an industrial water and said reaction product is present in an amount of 0.5 to 5 gm/m³ and said organic phosphonic acid complex former is present in an amount of from 0.2 to 20 gm/m³.

16. The process of claim 13 wherein said organic phosphonic acid complex-former is a mixture of 1-hydroxyethane-1,1-diphosphonic acid and aminotri-(methylene-phosphonic acid) in a weight ratio of 4:1 to 1:4.

17. A surfactant mixture composition consisting essentially of at least one surface-active compound selected from the group consisting of anionic surface-active compounds, nonionic surface-active compounds and zwitterionic surface-active compounds, in combination with a reaction product of ε-caprolactam with vicinal hydroxyalkamines which are derived from terminal mono-olefins or mixtures of mono-olefins with statistically distributed nonterminal double bonds and possible adducts thereof with epoxyalkanes having the overall formula:

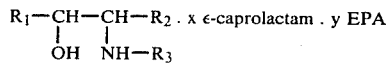

wherein $R_1$ and $R_2$ are members selected from the group consisting of hydrogen and alkyl having 1 to 16 carbon atoms with the proviso that the sum of the carbon atoms in $R_1$ and $R_2$ is from 8 to 16 when $R_1$ and $R_2$ are alkyl and from 8 to 16 when $R_1$ or $R_2$ is hydrogen, $R_3$ is a member selected from the group consisting of hydrogen, alkyl having 1 to 5 carbon atoms and

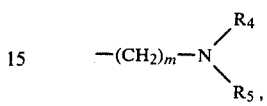

where m is an integer from 2 to 10, and $R_4$ and $R_5$ are members selected from the group consisting of hydrogen and alkyl having 1 to 3 carbon atoms, EPA is an epoxide selected from the group consisting of ethylene oxide, propylene oxide and glycide, x is a number representing mols of from 1.5 to 3.5, and y is a number representing mols of from 0 to 5; and the organic and inorganic acid salts thereof; the weight ratio of said at least one surface-active compound to said reaction product being from 50:1 to 2:1.

18. The surfactant mixture composition of claim 17 wherein said weight ratio is from 30:1 to 2:1.

19. The reaction product of claim 1 wherein $R_3$ is methyl.

20. In the process of washing textiles at temperatures or from 15° C. to 60° C. in the presence of a detergent composition including surface-active compounds and recovering cleaned textiles, the improvement consisting of employing the surfactant mixture composition of claim 17, as said surface-active compounds.

* * * * *

UNITED STATES PATENT AND TRADEMARK OFFICE
CERTIFICATE OF CORRECTION

PATENT NO. : 4,150,024
DATED : December 12, 1979
INVENTOR(S) : ANDREAS SYLDATK et al It is certified that error appears in the above–identified patent and that said Letters Patent are hereby corrected as shown below:

Column 1, line 11, "proper ties" should read -- properties --

Column 7, line 2, "acic" should read -- acid --.

Column 27, lines 36-37, the formula should read:

-- $R_1\text{-CH-CH-}R_2 \cdot x\ \varepsilon\text{-caprolactam}$ --.
$\quad\quad\ \ |\ \ \ |$
$\quad\quad\text{OH NH-}R_3$ Column 28, line 33, "1 to 5" should read -- 1.5 to 3.5 --.

Signed and Sealed this

Eighteenth Day of March 1980

[SEAL]

Attest:

SIDNEY A. DIAMOND

Attesting Officer

Commissioner of Patents and Trademarks